United States Patent [19]
Bookbinder et al.

[11] Patent Number: 6,093,559
[45] Date of Patent: Jul. 25, 2000

[54] PRODUCING LOW BINDING HYDROPHOBIC SURFACES BY TREATING WITH A LOW HLB NUMBER NON-IONIC SURFACTANT

[75] Inventors: Dana Craig Bookbinder, Corning; Edward John Fewkes, Jr., Horseheads; James Arthur Griffin, Corning; Frances M. Smith, Elmira; David L. Tennent, Campbell, all of N.Y.

[73] Assignee: Corning Incorporated, Corning, N.Y.

[21] Appl. No.: 08/918,354

[22] Filed: Aug. 26, 1997

Related U.S. Application Data

[60] Provisional application No. 60/029,009, Oct. 24, 1996.

[51] Int. Cl.$^7$ .............................. C12N 9/00; G01N 33/53; C07K 17/00; C07H 21/00
[52] U.S. Cl. .................................. 435/183; 435/2; 435/4; 435/41; 435/325; 435/243; 435/283.1; 435/289.1; 435/307.1; 436/547; 530/300; 530/350; 536/22.1
[58] Field of Search .................................. 435/4, 41, 174, 435/177, 180, 181, 183, 2, 325, 243, 283.1, 289.1, 307.1; 530/402, 810, 812, 815, 816, 300, 350; 536/22.1

[56] References Cited

U.S. PATENT DOCUMENTS

| | | | |
|---|---|---|---|
| 5,248,620 | 9/1993 | Sluka et al. | 436/531 |
| 5,258,129 | 11/1993 | Kato et al. | 252/8.9 |
| 5,500,254 | 3/1996 | Quincy, III et al. | 427/387 |
| 5,516,703 | 5/1996 | Caldwell et al. | 436/532 |
| 5,525,415 | 6/1996 | Quincy, III et al. | 428/266 |
| 5,540,984 | 7/1996 | Quincy, III et al. | 428/266 |

FOREIGN PATENT DOCUMENTS

WO 94/03544 7/1993 WIPO.

OTHER PUBLICATIONS

J.S. Tan, D. E. Butterfield, C.L. Voycheck, K.D. Caldwell and L. T. Li, entitled "Surface Modificaiton of Nanoparticles by PEO/PPO Block Copolymers to Minimize Interactions with Blood Components and Prolong Blood Circulation in Rats" Biomaterials 1993, vol. 14, No. 11, pp. 823–833.

Jenq–thun Li, Jan Carlsson, Shao–Chie Huang and Karin D. Caldwell, entitled "Adsorption of Poly(Ethylene Oxide-)–Containing Block Copolymers" Aug. 22–27, 1993, pp62–78, Advances In Chemistry Series 248, American Chemical Society, Washington D.C.

J.D. Andrade, Interfacial phenomena and biomaterials, Medical Instrumentation, Mar.–Apr. 1973, vol. 7, No. 2, pp. 110–120.

J.D. Andrade Surface and Interfacial Aspects of Biomedical Polymers, 1985, Vol. 2, Protein Absorbtion, pp. 1–80, Adsorption, Edited by Joseph D. Andrade (1985).

Mansoor Amiji and Kinam Park, Prevention of protein adsorption and platelet adhesion on surfaces by PEO/PPO/PEO Triblock Copolymers, Dec. 12, 1991, vol. 13, No. 10, pp. 682–692.

Editorial Board—H. Mark, D. Othmer, C. Overberger, G. Seaborg (No autho listed) Encyclopedia of Chemcial Technology, Surfactants and Detersive Systems, No date, vol. 22, Third Edition, Kirk–Othmer, pp. 332–335.

Jin Ho Lee, J. Kopeck, J.D. Andrade, Protein–resistant surfaces prepared by PEO–containing block copolymer surfactants, Journal of Biomedical Materials Research, 1989, vol. 23, pp 351–368 (89).

Jin Ho Lee, P. Kopeckova, J. Kopecek and J.D. Andrade, Surface properties of copolymers of alkyl methacrylates with methoxy (polyethylene oxide) methacrylates and their application as protein–resistant coatings, Biomaterials 1990, vol. 11, Sep., pp. 455–464.

Jin Ho Lee, J. Kopecek, J.D. Andrade, Surface Properties of Aqueous PEO–contianing Block Copolymers Srfactants Protein–Resistant Surfaces, p. 613–617.

H. Thurow and K. Geisen, Stabilisation of dissolved proteins against denaturation at hydrophobic interfaces, , Diabetologia 1984, pp. 212–218.

No author, Polymer Surfactants, Plastic Additives, Henkel Corporation, Jan. 1993 pp 1–48.

Jin Ho Lee, Hai Bang Lee, J.D. Andrade, Blood Compatibility of Polyethylene Oxide Surfaces, 1995, vol. 20, pp. 1043–1079.

E. Merrill, E. Salzman, Polyethylene Oxide as a Biomaterial, Apr./Jun. 1995, ASAIO Journal, vol. 6, pp. 60–64.

T. Okano, M. Uruno, N. Sugiyama, M. Shimdada, I. Shinohara, K. Kataoka Y. Sakurai, Suppression of platelet activity on microdomain surfaces of 2–hydroxyethyl methacrylate–polyether block copolymers, Journal of Biomedical Materials Research, (1986) vol. 20, pp 1035–1047.

A. Okkema, T. Grasel, R. Zdrahala, D. Solomon, S. Cooper, Bulk, surface, and blood–contacting properties of polyetherurethanes modified with polyethylene oxide, 1989, Biomater, Sci. Polymer Edn. vol. 1, No. 1, pp 43–62.

(List continued on next page.)

*Primary Examiner*—David M. Naff
*Attorney, Agent, or Firm*—Thomas R. Beall

[57] ABSTRACT

Hydrophobic polymer surfaces whose level of protein binding is less than about 50–80 ng/cm$^2$ are achieved by: (1) applying to a hydrophobic polymer surface a coating solution composed of a solvent and a non-ionic surfactant having a HLB number of less than 5 and at least one hydrophilic element which can extend into an aqueous solution; and (2) drying the surface to remove the solvent and thereby bring the surfactant into direct contact with the hydrophobic polymer. The combination of a low HLB number and the drying step have been found to produce low binding surfaces which can withstand multiple washes with water and/or protein-containing solutions. Alternatively, the low binding surfaces can be produced by applying the non-ionic surfactant to mold surfaces which contact molten polymer and form the polymer into a desired shape, e.g., into a multi-well plate, a pipette tip, or the like. Further, the low binding surfaces may be produced by incorporating non-soluble, non-ionic surfactants having an HLB number of less than or equal to 10 into a polymer blend prior to molding the article.

23 Claims, No Drawings

OTHER PUBLICATIONS

N. Owens, D. Gingel, P. Rutter, Inhibition of cell adhesion by a synthetic polymer adsorbed to glass shown under defined hydrodyanmic stress, 1987, Journal of Cell Science, pp 667–675.

K. Prime, G. Whitesides, Adsorption of Proteins onto Surfaces Containing End–Attached Oligo (ethylene oxide): A Model System Using Self–Assembled Monolayers, Jul. 8, 1993 American Chemical Society, pp. 10714–10721.

B. E. Rabinow, Y.S. Ding, C. Qin, M.L. McHalsky, J.H. Schneider, K.A. Ashline, T.L. Shelbourn, R.M. Albrecht, Biomaterials with permanent hydrophilic surfaces and low protein adsorption properties, Dec. 9, 1994, Biomater Sci, Polymer Edn, Vol. 6 No. 1 pp 91–109.

F.E. Regnier, R. Noel, Glycerolpropylsilane Bonded Phases in the Steric Exclusion Chromatography of Biological Macromolecules, (1976) Journal of Chromatographic Science, vol. 14, pp 316–320.

C.G.P.H. Schroën, M.C. Wijers, M.A. Cohen–Stuart, A. van der Padt, K. van't Riet, Membrane modification to avoid wettability changes due to protein adsorption in an emulsion/membrane bioreactor, (1993) Journal of Membrane Science 80, pp 265–274.

M. S. Sheu, A.S. Hoffman, J. Feijen, A. glow discharge treatment to immobilize poly(ethylene oxide)/poly (propylene oxide) surfactants for wettable and non–fouling biomaterials, Adhesion Sci. Tech vol. 6 No. 9 pp 995–1009 (1992).

M.S. Sheu, A.S. Hoffman, B.D. Ratner, J. Feijen, J.M. Harris, Immobilization of polyethylene oxide surfactants for non–fouling biomaterial surfaces using an argon glow discharge treatment, J. Adhesion Sci. Technol, vol. 7, No. 10, pp. 1065–1076 (1993).

M. Shimada, M. Miyahara, H. Tahara, I. Shinohara, T. Okano, K. Katoaka, Y. Sakurai, Synthesis of 2–Hydroxethyl Methacrylate–Dimethylsiloxane Block Copolymers and Their Ability to Suppress Blood Platelet Aggregation, Polymer J., vol. 15, No. 9, 1983.

PRODUCING LOW BINDING HYDROPHOBIC SURFACES BY TREATING WITH A LOW HLB NUMBER NON-IONIC SURFACTANT

This application claims the benefit U.S. Provisional Application No. 60/029,009, filed Oct. 24, 1996.

FIELD OF THE INVENTION

This invention relates to methods for reducing the binding of organic materials (e.g., peptides, proteins, nucleic acids, and cells) to hydrophobic surfaces (e.g., polymeric surfaces). The invention also relates to articles of manufacture (e.g., labware) having such low binding surfaces.

BACKGROUND OF THE INVENTION

Biological materials such as peptides, proteins, nucleic acids, and cells are often stored or transferred in containers such as centrifuge tubes and pipettes made of plastic or other hydrophobic materials. It is a common observation that biological compounds adsorb/bind to the surfaces of such containers. This is also true for organic materials which exhibit some hydrophobicity in an aqueous solution, e.g., acridinium compounds, PCBs, etc..

For many applications, such binding is undesirable. For example, the binding results in the loss of valuable materials, such as, enzymes and antibodies, and can result in variations in the dispensing of organic materials, especially when small volumes are involved. The binding of proteins, cells, and platelets to hydrophobic surfaces is also of concern in a variety of blood handling procedures.

As a result of these considerations, extensive efforts have been made to provide methods for reducing the binding of proteins and other organic compounds to hydrophobic surfaces. Examples of the approaches which have been considered can be found in Caldwell et al., U.S. Pat. No. 5,516,703; Ding et al., International Application Publication WO94/03544; Amiji et al., *Biomaterials,* 13:682–692, 1992; J. Andrade, "Principles of Protein Adsorption" in *Surface and Interfacial Aspects of Biomedical Polymers,* J. Andrade, editor, Volume 2, Plenum Press, New York, 1–80, 1985; Lee et al., *Polymeric Mater. Sci Eng.,* 57:613–617, 1987; Lee et al., *Journal of Biomedical Materials Research,* 23:351–368, 1989; Lee et al., *Biomaterials,* 11:455–464, 1990; Lee et al., *Prog. Polym. Sci.,* 20:1043–1079, 1995; Merrill et al., *ASAIO Journal,* 6:60–64, 1983; Okano et al., *Journal of Biomedical Materials Research,* 20:1035–1047, 1986; Okkema et al., *J. Biomater. Sci. Polymer Edn.,* 1:43–62, 1989; Owens et al., *Journal of Cell Science,* 87:667–675, 1987; Rabinow et al., *J. Biomater. Sci. Polymer Edn.,* 6:91–109, 1994; Schroën et al., *Journal of Membrane Science,* 80:265–274, 1993; Sheu et al., *J. Adhesion Sci. Technol.,* 6:995–1009, 1992; Shimada et al., *Polymer Journal,* 15:649–656, 1983; and Thurow et al., *Diabetologia,* 27:212–218, 1984.

The criteria which a successful technique for producing a low binding surface should satisfy include: 1) a sufficiently low level of binding; 2) substantial permanence; 3) ease of use; and 4) low cost. It is the goal of the present invention to provide methods for producing low binding surfaces which satisfy all of these criteria.

SUMMARY OF THE INVENTION

The present invention achieves the above criteria through the combination of specific coating materials and specific process steps, both of which are critical to the success of the technique.

The specific materials employed in the invention are non-ionic surfactants which have a hydrophilic element which can extend into an aqueous solution, e.g., a hydrophilic end group, and have a hydrophilic-lipophilic balance number (HLB number) which is less than or equal to 5. The term "non-ionic surfactant" is used herein in accordance with its classical definition as a molecule containing two structurally dissimilar groups having different solubilities in an aqueous solution. See *Kirk-Othmer Encyclopedia of Chemical Technology,* Third Edition, Volume 22, page 332, John Wiley & Sons, New York, New York, 1983.

As demonstrated in the examples presented below, a HLB number less than or equal to 5 has been found critical to achieve a durable low binding surface. Although non-ionic surfactants have been previously considered for use in producing low-binding surfaces (see the references cited above), the criticality of a HLB number less than or equal to 5 has not previously been recognized. As the present invention demonstrates, above this number, protein binding is either not substantially inhibited or is only temporally inhibited, while at or below the number, long term inhibition of protein binding is achieved.

One specific process employed in the invention comprises the steps of applying the non-ionic surfactant to the surface (substrate) in a solvent and then drying the surface (substrate) to remove the solvent and thereby bring the surfactant into direct contact with the surface so as to bind thereto. Preferably, the surface is fully dried. The applying and drying steps must be performed without an intermediate washing step with an organic solvent.

As demonstrated in Examples 7 and 8, the drying step is critical to obtaining a durable low-binding surface. Without this step, the non-ionic surfactant can be removed from the hydrophobic surface by aqueous solutions, thus causing the surface to lose its low-binding properties. Such removal occurs even if a non-ionic surfactant having a HLB number less than or equal to 5 is used. However, once the coating has been dried onto the surface, it becomes effectively permanent and is not substantially removed by contact with an aqueous solution. This is an important advantage of the invention since the low-binding surfaces which the art desires are for use with aqueous solutions.

The avoidance of any washing with an organic solvent prior to the drying step is important in view of the low HLB numbers of the non-ionic surfactants used in the practice of the invention. Those low HLB numbers make the non-ionic surfactant substantially soluble in organic solvents, so that washing with such a solvent will remove essentially all of the surfactant from the surface, thus preventing the surfactant from performing its low-binding function.

Those references which have employed non-ionic surfactants having HLB numbers less than or equal to 5 have not disclosed, suggested, or in any way recognized the criticality of the above process steps. Specifically, the Thurow et al. and Schroën et al. references cited above each use at least one non-ionic surfactant having a HLB number less than 5. In particular, Thurow et al.'s preferred Genapol PF-10 material has a HLB number of less than 5, as does Schroën et al.'s L-92 material. While Thurow et al report that Genapol PF-10 prevents adsorption of insulin to latex particles, Schoën et al. report that L-92 does not prevent adsorption of lipase to a polypropylene membrane. Significantly, neither reference describes drying the non-ionic surfactant onto a hydrophobic surface, and thus neither can produce a low-binding surface which is substantially permanent, as is required for a practical product.

Sheu et al also use non-ionic surfactants having low HLB numbers (i.e., PLURONIC 121, 122, and 127), but employ a complicated argon glow discharge process to bind these surfactants to a hydrophobic surface, namely, low density polyethylene (LDPE). In certain experiments, they omitted the glow discharge treatment and instead merely applied the surfactants to LDPE and washed with chloroform (see their FIG. 2). Under these conditions, they reported no reduction in protein binding compared to untreated LDPE (see their page 1006). Given this conclusion, Sheu et al. clearly did not recognize that low HLB surfactants could be successfully used to produce low-binding surfaces without the need for glow discharge treatment, as demonstrated by the present invention.

The process steps of the invention, i.e., applying the surfactant in a solvent and then drying to remove the solvent, are plainly easy to perform. The process is also inexpensive since only very low concentrations of surfactant are needed to achieve a low-binding surface. For example, one pound of surfactant which costs about a dollar (U.S.), can provide a micron thick coating on about 5,000 square feet (465 square meters) of hydrophobic surface. The invention thus satisfies each of the above four criteria for a practical process for producing a low-binding surface, i.e., it provides a low cost, easy-to-use procedure for providing a substantially permanent, low binding surface.

In certain embodiments, the invention can be made even simpler and less expensive. In these embodiments, the low-binding surface is created at the same time the part which is to have such a surface is formed. Specifically, in accordance with these embodiments, a surfactant having the characteristics described above, i.e., a HLB number less than or equal to 5 and a hydrophilic element which can extend into an aqueous solution, is applied to the mold used to make the part by, for example, spraying a solution of the surfactant onto at least one of the mold's molding surfaces. In accordance with the invention, it has been found that when such a treated mold is used to make parts, a sufficient amount of surfactant is transferred from the mold to the surface of the part so as to produce a low-binding surface. Although the mold can be sprayed with the surfactant each time a part is made, less frequent spraying can be used if desired. As with the post formation procedures described above, these as-the-part-is-made procedures satisfy all of the criteria for a practical process for producing a low-binding surface.

Further, it has been found, that in certain embodiments, surfactants having an HLB number of less than or equal to 10 can be blended in with a number of base polymer thermoplastics prior to molding. A sufficient number of low HLB number molecules migrate to the surface during the molding process, a process called "blooming", to yield a low binding surface.

The process employed in this embodiment comprises the steps of thoroughly mixing the non-water soluble non-ionic surfactant with a matrix polymer into a blend, melting the blend, and exposing the blend to sheer conditions such that the non-ionic surfactant will move to the surface of the polymer substrate through sheer. For example, an extruder may be used to blend the materials and an injection molding machine may be used to transform the polymer blend into a finished part. Once the non-ionic surfactant has migrated to the surface of the polymer, the hydrophilic element of the surfactant molecule extends from the polymer surface into an aqueous solution. The resultant product exhibits the non-binding characteristics consistent with products that have been coated with the surfactant. An advantage of using the blending process lies in the elimination of the drying step and the coating step, thereby further aiding in cost reduction.

Ding et al. discloses the use of polymer blends containing water-soluble polymers for creating a low protein binding surface on a substrate polymer. However, Ding et. al. does not disclose the addition of non-ionic, non-water soluble surfactants having an HLB number less than or equal to 10, to a polymer blend.

A particularly advantageous application of the invention is in the production of labware having protein resistant surfaces. Examples of the types of products which can be provided with low-binding surfaces in accordance with the invention include containers of all shapes, sizes, and descriptions, multiwell strips, pipettes, pipette tips, membranes, reagent reservoirs, storage vessels, tubing and the like. Once provided with a low binding surface, these products can be sterilized using conventional techniques such as gamma-ray sterilization.

DESCRIPTION OF THE PREFERRED EMBODIMENTS

As discussed above, the present invention relates to the creation of low-binding surfaces on hydrophobic substrates through the use of non-ionic surfactants having a HLB number less than or equal to 5 (less than or equal to 10 for use in polymer blends) and a hydrophilic element which can extend into an aqueous solution. Discussions of HLB numbers and how they are determined for specific surfactants can be found in, for example, the publication of ICI Surfactants entitled *The HLB System* and, in particular, in Chapter 7 of that publication entitled "How to Determine HLB of an Emulsifier" (ICI Americas, Inc., Wilmington, Del., 1992).

The non-ionic surfactant used in the practice of the invention needs to have a hydrophilic element which can extend into an aqueous solution so as to provide the requisite low-binding surface. Although not wishing to be bound by any particular theory of operation, it is believed that such a hydrophilic element when hydrated and extending away from a hydrophobic surface provides an aqueous boundary layer which cannot be readily penetrated by molecules having hydrophobic regions, e.g., proteins, thus preventing such molecules from binding to the hydrophobic surface. In many cases, the non-ionic surfactant molecules used in the practice of the invention will have a central hydrophobic region connected at each end to a hydrophilic element which can extend into an aqueous solution. In other cases, the molecules will have a hydrophobic region connected on only one end to a hydrophilic element. Surfactant molecules having other configurations can, of course, be used if desired provided they have at least one hydrophilic element which can extend into an aqueous solution. It should be noted that in the limit, the hydrophilic element can be as simple as a hydroxyl group as demonstrated by the low binding achieved with polyproylene oxide (see Example 6 below).

The presence of the hydrophilic element or elements means that the surfactant molecules will normally have a HLB number greater than zero, i.e., they will have some hydrophilic character. (Note that in the case of polypropylene oxide, the HLB number is in effect close to zero, i.e., it is less than 0.5.) However, since the HLB number must be less than or equal to 5 to achieve a substantially permanent, low-binding surface, this hydrophilic character is significantly less than the molecule's lipophilic character. Generally, non-ionic surfactants having HLB numbers less than about 2.5 are preferred for the practice of the invention.

A variety of non-ionic surfactants now known or subsequently developed can be used in the practice of the invention. Examples of suitable surfactants include alkyl alcohol ethyoxylates, alkyl ester ethyoxylates, sorbitol alkyl esters, glycerol alkyl esters, and ethylene oxide/propylene oxide block co-polymers. As discussed above, polypropylene oxide can also be used in the practice of the invention. Preferably, the polypropylene oxide will have an average molecular weight in the range of from about 1,000 to about 15,000. Derivatives of polypropylene oxide, such as branched and star polymers, can also be used in the practice of the invention.

These and other suitable surfactants can be obtained from a variety of manufacturers including ICI Americas, Inc., Wilmington, Del.; BASF Corp., Parsippany, N.J.; Witco Corp., Greenwich, Conn.; and the Henkel Corporation Ambler, Pa. If desired, mixtures of non-ionic surfactants can be used in the practice of the invention, provided each surfactant used in the mixture has a HLB number less than 5. Lists of various commercially available non-ionic surfactants can be found in *McCutcheon's Emulsifiers and Detergents,* North American edition, The Manufacturing Confectioner Publishing Co., Glen Rock, N.J., 1995. A preferred non-ionic surfactant for use in the present invention is Pluronic® L-121.

A variety of hydrophobic surfaces can be made low-binding in accordance with the invention. As used herein, a surface is considered to have been made low binding if the ratio of protein binding before treatment to that after treatment is less than about 0.5 and preferably less than about 0.3. Similarly, a surface treatment is considered to be substantially permanent if the treated surface retains its low protein binding properties after at least about 2 water washes at room temperature and preferably after at least about 6 washes, again at room temperature, where a water wash as used herein lasts at least 60 seconds.

Examples of the types of polymeric surfaces which can benefit from the invention include those comprising or composed of polystyrene, polypropylene, polymethyl methacrylate, polyvinyl chloride, polymethyl pentene, polyethylene, polycarbonate, polysulfone, polystyrene copolymers (e.g., SAN and ABS), polypropylene copolymers, fluoropolymers, polyamides, silicones, and elastomers, including silicone, hydrocarbon, and fluorocarbon elastomers. Other materials can be treated provided they have a hydrophobic surface to which the surfactant can bind.

The non-ionic surfactants are applied to the hydrophobic surface in the form of a coating solution comprising the surfactant and a solvent. In view of the surfactant's low HLB number, the solvent is typically an organic solvent, a mixture of organic solvents, or a mixture of water and one or more miscible organic solvents, e.g., a water/alcohol mixture. To facilitate the drying step, the solvent should be one that can be easily evaporated. Solvents which are primarily composed of water are not preferred, although they can be used if desired. Such solvents evaporate relatively slowly and can lead to agglomeration problems in view of the low HLB number of the surfactant. Also, when used to spray a mold, any water which has not evaporated by the time the mold is closed and molten polymer is injected, will likely cause defects in the finished part.

The concentration of the surfactant in the coating solution can vary quite widely depending upon the application. Convenient concentrations are in the range of from about 0.01% weight per volume to about 1.0% weight per volume. A suitable concentration for the post formation coating of labware is about 0.1% weight per volume. Higher or lower concentrations can, of course, be used if desired.

The coating solution can be applied to the hydrophobic surface using a variety of techniques, examples of which include spraying, dipping, brush coating, and the like. A small quantity of surfactant can be used to treat a large surface area. Accordingly, the volume of coating solution applied per square millimeter of hydrophobic surface can be quite small, e.g., about 2 to 20 microliters per $cm^2$ for a coating solution having a surfactant concentration of about 0.1% weight per volume. The amount of surfactant per unit area and the corresponding coating solution concentration and application rate can be readily determined for any particular application by examining test pieces of the hydrophobic surface to determine if the requisite reduction in binding has been achieved.

The drying of the coating solution can be performed at room temperature at ambient pressure. Higher or lower temperatures can be used if desired. It was found that higher temperatures (50–70° C.) can sometimes facilitate a more uniform coating of the surface., Reduced pressures can be employed if fast drying is needed. Whatever drying procedure is adopted, it needs to remove sufficient solvent so that the non-ionic surfactant comes into direct contact with the hydrophobic surface so as to bind to that surface. That such binding has occurred can be readily tested by repeated washing of the coated surface with an aqueous solution. If the surface retains its non-binding properties after such washing, the requisite binding has been achieved; if not, more thorough drying of the coated surface is needed.

As discussed above, rather than being applied to finished parts, the non-ionic surfactants of the invention can be applied to the mold used to form the part. In accordance with these embodiments, all or a portion of the mold surface is sprayed with a solution containing the non-ionic surfactant, the mold is closed, molten polymer is injected into the mold and cooled, the mold open is opened, and the molded part is ejected from the mold. The solution used to coat the mold can have the same composition as the coating solutions discussed above. In accordance with the invention, it has been found that sufficient surfactant is transferred to the surface of the polymer to produce a substantially permanent, non-binding surface. Although spraying is preferred, other techniques, e.g., brush coating, can be used to apply the surfactant to the mold. Equipment of the type used to apply release agents to molds can be used to apply the surfactant.

In producing non-binding surfaces by adding the non-ionic surfactant to the blend prior to molding, the ionic surfactant molecules were blended at 5% into a base polymer. The required amount of non-ionic surfactant to be added to the matrix polymer may vary depending on the molecule, anywhere within a preferred range of 0.10–10.0% (weight/volume), and more preferably between 0.5–5.0%. It should be noted that other additives such as dyes, pigments, stabilizers, impact modifiers and the like may be added to the blend to create a finished product having certain desired characteristics.

Without intending to limit it in any manner, the present invention will be more fully described by the following examples. The materials and methods which are common to the examples are as follows.

Materials and Methods

Table 14 sets forth the non-ionic surfactants used in the examples along with their HLB numbers and their commercial tradenames where applicable.

Except where indicated, the non-ionic surfactants were applied to the hydrophobic surfaces being tested as a 0.1% (weight/volume) solution in isopropanol. A sufficient amount of coating solution was used to cover the surface being testing with a thin layer of the solution (e.g., 25 μl of the solution per well for a standard 24-well plate). In some cases, the solution was applied to surface by spraying; in others, it was poured onto the surface (into the well). Except where indicated, coated samples were either dried at 70° C. for 30 minutes in an air circulated oven or dried at room temperature overnight to evaporate the isopropanol.

Protein binding was determined in some examples using a colloidal gold straining procedure. In accordance with this procedure, colloidal gold becomes electrostatically attached to bound protein and is detected by measuring absorbance at 550 nanometers. Bio-Rad Laboratories' Colloidal Gold Total Protein Stain was used for this purpose, with absorbance being measured with a Cambridge Technologies Plate Reader (No. 7520).

As generally understood in the art, the upper limit for a low binding surface is about 50–80 ng/cm$^2$. For comparison, medium binding, such as that exhibited by untreated polystyrene or polypropylene, is around 200–400 ng/cm$^2$, and high binding, such as that exhibited by a polystyrene or polypropylene surface which has been plasma oxidized and gamma radiation sterilized, is around 400–800 ng/cm$^2$.

The designations "NA" and "ND" used in some tables mean "not applicable" and "not determined," respectively. The designation "PS" means polystyrene. The designation "M.W." means average molecular weight.

EXAMPLE 1

Radiometric Determination of Reduced Protein Binding

This example demonstrates by means of a radiometric readout that non-ionic surfactants can reduce the binding of protein to hydrophobic surfaces.

The hydrophobic surfaces used were flat bottom microtiter plates composed of high binding polystyrene (Corning Costar No. 2581) and medium binding polystyrene (Corning Costar No. 2587). Testing was performed with and without gamma radiation sterilization using cobalt 60 (1.5 Mrad).

The non-ionic surfactants used in this example are set forth in Table 1. The surfactants were applied to the test plates as described in Materials and Methods, followed by sterilization where indicated.

Levels of protein binding were determined using a radiolabeled protein, namely, $^{125}$I-IgG (goat anti-mouse) purchased from DuPont/NEN. Unlabeled IgG in sodium carbonate buffer pH 9.2 was spiked with $^{125}$I-IgG so that the final concentration of labeled IgG and cold IgG in the test solution was 10 μg/mL.

Aliquots of 0.1 milliliters of the protein solution were placed in quadruplicate in the wells of 8-well strips removed from the test microtiter plates. The wells were incubated overnight at 4° C. with shaking. The supernatants were removed from the wells, followed by three washes with 0.2 mL of PBS. The wells were then dried and individually counted to determine "total" IgG binding. After determining "total" binding, the wells were incubated for two hours in 0.2 mL of PBS-Tween (0.05%) at room temperature with shaking. The supernatants were removed from the wells followed by three washes with 0.2 mL of PBS. The wells were dried and individually counted to determine "tight" IgG binding.

Untreated high binding and medium binding plates were used as controls. A comparative experiment was also performed in which a BSA protein coating was used in place of a surfactant coating. The BSA was preabsorbed onto the walls of the wells and then washed to remove excess material. Testing was then performed using the radiolabeled IgG solution as described above.

Radiolabel measurements were performed in a double blind study at BioMolecular Assays (Woburn, Mass.). IgG binding values per microwell were converted to ng/cm$^2$ values using a surface area of 0.94 cm$^2$ for a 0.1 mL volume.

As shown in Table 1, the non-ionic surfactants tested each resulted in a substantial decrease in protein binding in comparison to the two controls and the BSA experiment, with the binding after sterilization being greater in most, but not all, cases, but still significantly reduced from the controls.

EXAMPLE 2

Enzymatic Determination of Reduced Protein Binding

This example demonstrates by means of an enzymatic readout that non-ionic surfactants can reduce the binding of protein to hydrophobic surfaces.

The non-ionic surfactants used in this example are set forth in Table 2. The surfactants were coated onto a medium binding polystyrene plate (Corning Costar No. 2587) as described in Material and Methods. A medium binding polystyrene plate (Corning Costar No. 2587) and a high binding polystyrene plate (Corning Costar No. 2581) were used as controls.

The reagents employed in this example were:
(a) HRP-Goat A'Mouse IgG: Kirkegaard & Perry Laboratories, Inc. Catalog No. 074-1806. Stock solution: 0.5 mg/ml; working concentration: 0.04 μg/ml. The working concentration was obtained by adding 11 μl of the stock solution per 25 mls of PBS pH 7.4 to produce a work stock (WS), and then diluting 1:6 (i.e., 10 mls WS+50 mls PBS pH 7.4).
(b) Phosphate Buffered Saline: Sigma 1000-3. Buffer preparation: 2 packages PBS per 2 liters H$_2$O.
(c) Wash solution 20× Concentrate: Kirkegaard & Perry Laboratories, Inc. Catalog No. 50-63-01. Wash concentration: 1 M (3800 mls H$_2$O+200 mls wash solution concentrate).
(d) ABTS Peroxidase Substrate & Peroxidase Solution B: Kirkegaard and Perry Laboratories, Inc. Catalog Nos. 50-64-02 & 50-65-02.
(e) Sodium Lauryl Sulfate (SDS): Sigma Catalog No. L-4509. Stop solution: 1% SDS (10 gm SDS per 1 liter H$_2$O).

The procedures employed were:
(1) 100 μl/well of HRP-Goat A'Mouse IgG at a concentration of 0.04 μg/ml were added to the test wells and incubated for 1 hour at room temperature.
(2) The wells were then washed 5 times with the 1M wash solution. Each wash include a 5 minute soak followed by decanting.
(3) 100 μl/well of substrate (30 mls ABTS+30 mls H$_2$O$_2$) were added to the test wells and incubated for 15 minutes at room temperature in the dark.
(4) 100 μl/well of stopping solution (1% SDS) were added to the test wells.
(5) The plates were then shaken and read at 405 nm.
(6) Reduction in binding was determined by comparing the absorbance measured in step (5) with the absorbance measured for a high binding polystyrene plate which had not been treated with a non-ionic surfactant but otherwise subjected to steps (1) to (5).

As shown in Table 2 significant reductions in bound enzyme were achieved by the non-ionic surfactants, with most reductions being greater than 95%

EXAMPLE 3

Determination of Reduced Protein Binding by Colloidal Gold Staining

This example demonstrates by means of a colloidal gold readout that non-ionic surfactants can reduce the binding of protein to hydrophobic surfaces.

The non-ionic surfactants used in this example are set forth in Table 3. The surfactants were coated onto medium binding polystyrene plates (Corning Costar No. 2587) as described in Material and Methods.

The plates were incubated with IgG as follows: 0.1 ml of Horse IgG Pierce Labs) at a working concentration of 10 $\mu$g/ml in 0.10M NaHCO$_3$ buffer (pH9.4) were added to each well, incubated 30 minutes on a rocker table, and rinsed with dI H$_2$O. The plates were gold stained overnight (0.3ml/well), rinsed in dI H$_2$O, air dried, and absorbance was measured at 550 nm.

As shown in Table 3, the non-ionic surfactants clearly achieved low protein binding levels, i.e., undetectable levels by the colloidal gold staining procedure.

EXAMPLE 4

The Reduction in Protein Binding is pH Independent

This example demonstrates that non-ionic surfactants can inhibit protein binding over a wide range of pH's.

The non-ionic surfactants used in this example are set forth in Table 4. Polystyrene plates having 24 wells (Corning Costar #9447) were coated as described in Materials and Methods.

BSA protein (Bovine Serum Albumin, Fraction V, Sigma) was prepared at 10 $\mu$g/ml in 0.10 M acetate buffer (pH=4.6), in 0.10 M PBS (pH=7.4), and in 0.10 M NaHCO$_3$ buffer (pH=9.2). Wells of each coated plate, along with uncoated controls, were aliquoted 0.50 ml each of the protein solutions. The samples were run in triplicate.

The plates were placed on a rocker table for 30 minutes at 23° C. The protein solutions were then emptied from the plates, and the wells were rinsed three times with dl H$_2$O. Thereafter, 1.0 ml of colloidal gold stain was added to each well (see Materials and Methods). The plates were placed on a rocker table overnight, rinsed three times with dI H$_2$O, and air dried. Absorbance at 550 nm was then read using the Cambridge Technologies Plate Reader.

As shown in Table 4, the non-ionic surfactants were effective in preventing protein binding for a wide variety of pH's.

EXAMPLE 5

Reduced Cell Attachment

This example demonstrates that non-ionic surfactants can reduce cell attachment.

The procedures used were as follows. Polystyrene 24-well plates were coated with the non-ionic surfactants listed in Table 5 in accordance with the procedures described in Materials and Methods. Uncoated plates were used as a control. For comparison, plates with a covalently attached acrylamide coating (Corning Costar Catalog #2500) and with a stearic acid coating were also tested. The stearic acid coating was applied in the same manner as the non-ionic surfactants again using a 0.1% (w/v) solution.

The plates were gamma sterilized at 1.5 Mrad and then inoculated with 5.6×10$^4$ MDCK wells per well in 1 ml of complete media containing 5% FBS (Fetal Bovine Serum). Incubation was carried out at 37° C. in a 5% CO$_2$ atmosphere for two days. The plates were fixed and stained, and cell attachment was noted. Following this, the wells were stained using the colloidal gold technique to detect bound protein. Only Visual observations were made.

As shown in Table 5, various of the non-ionic surfactants of the invention achieved reduced cell binding and/or reduced protein binding.

Experiments were also performed with cells suspended in serum. The cells used in these experiments were MDCK cells. The surfactants used were the same as used in Table 5. Again, reduced binding of the cells to surfaces treated with a non-ionic surfactant was observed.

EXAMPLE 6

Requirement for a Hydrophilic Element Which Can Extend into an Aqueous Solution

This example demonstrates that the non-ionic surfactant used to produce a low binding surface must have a hydrophilic element which can extend into an aqueous solution.

A non-ionic surfactant can have a variety of structures, including a hydrophobic segment and a hydrophilic segment attached end-to-end, a central hydrophobic segment attached on each end to a hydrophilic segment, or a central hydrophilic segment attached on each end to a hydrophobic segment. These three molecular forms can have similar HLBs, but the first two variations have at least one hydrophilic endgroup whereas the third variation, with its hydrophilic segment in the center, has hydrophobic endgroups.

The non-ionic surfactants listed in Table 6 were tested for their ability to produce a low binding surface using the techniques described in Materials and Methods. Polystyrene was used as the hydrophobic test surface and IgG/Au staining was used as the readout.

As shown in Table 6, for similar HLB numbers, surfaces coated with surfactants having at least one hydrophilic endgroup are effective in inhibiting protein binding, while surfaces coated with surfactants that do not have a hydrophilic endgroup are ineffective in inhibiting protein binding. The need for a hydrophilic element which can extend into an aqueous solution is clear from this data.

It should be noted that a surfactant suitable for use in the present invention need not have a hydrophilic endgroup but may have one or more hydrophilic groups attached to a hydrophobic backbone anywhere along the backbone's length provided such group or groups can extend into an aqueous solution.

EXAMPLE 7

Drying a Surfactant-Coated Surface Is Critical to its Durability

This example demonstrates the criticality of drying a surfactant-coated surface in order to achieve a durable low binding surface. More particularly, the purpose of the experiments of this example was to determine if non-ionic surfactant molecules absorb to a polymer surface to form a durable coating during aqueous solution exposure or only after the molecules have been dried onto the surface.

Duplicate 24-well plates were prepared as follows. Individual wells were filled with 3 ml of non-ionic surfactants at 0.5% (weight/volume) in $H_2O$/isopropanol (90/10 weight/volume). The surfactants used are listed in Table 7.

The duplicate plates were incubated for 30 minutes at room temperature on a rocker table and then emptied. One plate was tapped out and then allowed to dry at room temperature in a hood. It was then rinsed 5× with dI $H_2O$. The second plate was not allowed to dry, but instead was immediately rinsed 5× with $H_2O$. The plates were then tested for protein binding by filling each well with 0.5 ml of IgG (horse) at 10 µg/ml in PBS buffer and incubating for 30 minutes on a rocker table at room temperature. The plates were then rinsed with dI $H_2O$ and stained overnight with colloidal Au.

The results are shown in Table 7. As clearly demonstrated by this data, it is necessary to dry the surfactant molecules onto the plate to provide a durable coating. The data also shows the importance of using a surfactant which has a low HLB number.

EXAMPLE 8

Effect of Rinsing Surfaces Exposed to Aqueous Solutions of Non-Ionic Surfactants This example demonstrates that while the drying step is critical to durability, it is not required to achieve a low binding surface.

Medium binding (catalog #2587) and high binding (catalog #2581) polystyrene 96-well plates (8-well strips) manufactured by Corning Costar were used as follows. Individual wells of duplicate strips were filled with 0.3 ml of non-ionic surfactant 0.1% (weight/volume) in $H_2O$/isopropanol (95/5 volume/volume). The surfactants tested are listed in Table 8. Strips were incubated for 30 minutes at room temperature on a rocker table. Strips were then emptied and tapped out.

A first strip set, containing one high binding strip and one medium binding strip, was not rinsed; a second strip set, again containing one high binding strip and one medium binding strip, was rinsed 5× with dI $H_2O$. Immediately following this procedure, each well was aliquoted 0.10 ml of GAM-IgG-HRP (goat-anti-mouse-IgG-horseradish peroxidase enzyme labeled antibody; Kirkegaard and Perry, Gaithersburg, Md., Catalog #074-1806) at 1.0 µg/ml in PBS buffer (pH=7.4). Strips were incubated for one hour at room temperature on a rocker table. Strips were then rinsed 5× with PBS buffer containing 0.02% Tween-20 followed by post rinsing with $H_2O$.

Bound antibody was measured colorimetrically using an ABTS substrate reagent kit (Kirkegaard and Perry catalog #50-62-01). 0.10 ml of the ABTS/$H_2O_2$ solution was added to each well. A blue color forms as the ABTS reacts with the $H_2O_2$ via the peroxidase enzyme carried by the bound antibody. Absorbance at 405 nm was measured on a Cambridge Technologies #7520 Plate Reader.

Table 8 sets forth absorbance data as measured approximately 2 minutes after the ABTS/$H_2O_2$ solution was added to the strip. This absorbance data shows that (1) rinsing prior to drying removed the non-ionic surfactants from the strips thus preventing them from providing a low binding surface, and (2) even without drying, the surfacants achieved low binding provided they were not rinsed away.

EXAMPLE 9

Determination of Coating Durability Using Water Washes

This example demonstrates the effect of HLB number on the durability of non-ionic surfactant coatings on polystyrene.

The non-ionic surfactants used in this example are set forth in Table 9. Polystyrene plates having 24 wells (Corning Costar #9447) were coated with these surfactants as described in Materials and Methods.

Durability was tested by adding dI $H_2O$ to the wells of a test plate (3.0 mls/well), following which the plate was placed on a rocker table. The rocker table times and temperatures, as well as the number of repetitions of the dI $H_2O$ treatment, are set forth in Table 9. The protein binding properties of the various plates were determined using a protein solution which for each well comprised 0.5 ml of IgG (10 µg/ml) in 0.1M $NaHCO_3$ pH 9.4 buffer. The protein solution was incubated with the plate on a rocker table for 30 minutes at 23° C., following which the plate was $H_2O$ rinse 3× (3 mls each time). The colloidal gold staining procedure described above was used to reveal bound protein. The staining comprised an overnight incubation on a rocker table at 23° C., a dI $H_2O$ rinse, drying at room temperature, and reading at 550 nm.

As shown in Table 9, surfactants having HLB numbers of 1.0, 1.8, 2.0, 4.3, and 4.7 were durable, while those having HLB numbers of 6.7 and above were not durable.

EXAMPLE 10

Determination of Coating Durability Using Protein Solution Washes

This example demonstrates the effect of HLB number on the durability of non-ionic surfactant coatings on polystyrene, polypropylene, polymethyl methacrylate, and a PVDF copolymer.

The non-ionic surfactants used in this example are set forth in Table 10. The procedures used were as follows. Injection molded assay plates (96-well format) were made from polystyrene, (STYRON Dow 685D), polypropylene (Exxon 9374), polymethyl methacrylate (ATO HAAS), and KYNAR FLEX 2800 PVDF copolymer (ATO HAAS). Each well was aliquoted 0.10 ml of IgG (Horse Standard, Pierce) at 10 µg/ml in 0.01 M PBS buffer (pH=7.4) and placed on a rocker table for 30 minutes at 23° C. The protein solution was then emptied from the wells and a fresh protein solution was aliquoted to each well and the entire procedure repeated a total of six times. The plates were then rinsed three times with dI $H_2O$ (0.3 ml/well). Colloidal Au stain was added to each well (0.3 ml/well) and the plates were placed on a rocker table overnight. Plates were then rinsed 3 times with dI $H_2O$, allowed to dry, and absorbance at 550 nm was measured using the Cambridge Technologies Plate Reader.

As shown in Table 10, the cutoff for a durable low binding surface is at a HLB number of 5, with non-ionic surfactants having a HLB number well above 5 showing substantial binding after the multi-wash procedure, surfactants at 6 or just below, showing a slight amount of binding, and surfactants below 5 (i.e., those having HLB numbers of 1.0, 2.0, and 4.3) showing essentially no binding. For those surfaces which did absorb protein, the Au stain was readily visible to the unaided eye. Also, the non-durable coatings often produced "splotchy" protein binding until repeated rinses removed the coating. For these coatings, high variability was observed even within one well.

Results similar to those reported in Table 10 were obtained when the same procedure was followed using repeated BSA protein rinses or just dI H$_2$O rinses, instead of IgG rinses.

EXAMPLE 11

Coating Stability in the Presence of Excess Protein

This example demonstrates that exposure to large quantities of protein does not destroy the low binding properties of a hydrophilic surface coated with a non-ionic surfactant having a low HLB number.

The following procedures were employed in this example. 24-well polystyrene plates were coated as described in Materials and Methods using 25 μl aliquots of 0.10% (w/v) sorbitol mono-oleate in isopropanol. Coverage of the sorbitol mono-oleate was calculated at 10 μg/cm$^2$. Each well of the plates was exposed to 1.0 ml of BSA protein (Pierce) at 2 mg/ml in PBS buffer (pH=7.4). The plates were incubated on a rocker table for 30 minutes at room temperature, the wells were emptied, and the protein exposure was repeated a total of six times. The plates were then rinsed 3 times with dI H$_2$O and stained with the colloidal gold stain overnight. Plates were then rinsed with dI H$_2$O, dried, and the absorbance of each well was measured at 550 nm on the Cambridge Technologies plate reader.

As shown in Table 11, even in the presence of a large excess of protein, the low binding coating (which is believed to be physically absorbed and held only by van der Waals' forces) remained durable.

Similar experiments were carried out using Pluronic L-121 and L-122, and similar low protein binding results were obtained.

EXAMPLE 12

Toxicity

In addition to effectively providing low binding surfaces, non-ionic surfactants generally have low toxicity.

Table 12 sets forth LD$_{50}$ values (grams/Kg of rat) for various non-ionic surfactants. For comparison, the LD$_{50}$ values for mineral oil, NaCl, and As$_2$O$_3$ are also included in this table. The low toxicity of non-ionic surfactants is evident from this data.

Cytotoxicity experiments were performed using MDCK cells. The non-ionic surfactants tested were Pluronic L-121, L-122, and P-123; Span 80 and 85; and Brij 30, 72 and 93. These molecules were coated onto 24-well plates (Corning Costar #9447) from 0.1%(w/v) in isopropanol. Untreated polystyrene and normal tissue culture treated polystyrene (Corning Costar #25820) 24-well plates were used as controls. All plates were incubated at 37° C. for 48 hours with 2 ml/well of complete DMEM media containing 10% Fetal Bovine Serum (FBS). This incubation was performed in order to extract any potentially toxic compounds from the coated surface into the cell growth serum. The FBS solutions were then transferred to tissue culture treated polystyrene and each well was inoculated with ≈2×10$^4$ cells/well of MDCK cells, and then incubated at 37° C. for 72 hours in a 5% CO$_2$ atmosphere. Cells were then stained with Gram Crystal Violet. All of the wells yielded confluent cell growth with normal cell morphology.

EXAMPLE 13

Reduced Loss of Enzymatic Activity

This example demonstrates that an enzyme loses less activity when stored in a vessel coated with a non-ionic surfactant than in an uncoated vessel.

Corning Costar polystyrene medium binding (#2587) and high binding (#2581) microtiter plates were used in this example. Medium binding plates were coated with sorbitol mono-oleate and PEO(2) mono-oleate using the techniques described in Materials and Methods, specifically, coating with a 0.1% (w/v) solution of the surfactant in isopropanol followed by drying for 24 hours before use.

Horseradish peroxidase enzyme (HRP) was purchased from Sigma. A solution of 20 ng/ml HRP in 0.01 M PBS (pH=7.4) was prepared. Aliquots of 0.1 ml were placed in six wells of 8-well strips of coated plates, uncoated medium binding plates, and uncoated high binding plates.

Samples were preincubated either for 0 or 90 minutes. Aliquots of 0.1 ml of a tetramethylbenzidine (TMB) peroxidase substrate system (Kirkegaard & Perry) were added to each well and absorbance at 405 nm of each well was monitored versus time using a Cambridge Technologies Inc. #7520 microplate reader.

The results were:

(1) When the TMB solution was added with a preincubation of 0 minutes, the enzyme activity of all four surfaces (i.e., the two surfactant coated surfaces, the uncoated medium binding surface, and the uncoated high binding surface) were identical within experiment error.

(2) When the enzyme was pre-incubated for 90 minutes in the uncoated high binding and medium binding plates, it lost ~60% and ~98% of its activity, respectively.

(3) When the enzyme was pre-incubated for 90 minutes in either of the coated plates, the loss in activity was essentially zero.

Similar results were observed when polypropylene plates were used instead of polystyrene plates.

It should be noted that this is a total solution assay, so that the effect being observed is not direct physical loss of protein (enzyme), but rather loss of biological activity.

EXAMPLE 14

This example illustrates the use of the non-ionic surfactants of the invention to produce a membrane having a low binding surface.

The experiments were performed using 0.45 micron PVDF membranes. The membranes were coated two times by immersion using 0.1% (weight/volume) of the following non-ionic surfactants in isopropanol: sorbitol mono-oleate, Pluronic® L-121, Pluronic® L-122, and Pluronic® L-123. The membrane was dried at room temperature after each of the two immersion coatings. The coated membranes were incubated with IgG 10 μg/ml in 0.1M PBS (pH 7.4) for 30 minutes at room temperature on an orbital shaker. The membranes were then rinsed three times with water in a clean plate, each rinse being performed for 5 minutes on the shaker. Thereafter, the membranes were stained with Au overnight, again on the shaker. An uncoated PVDF membrane was used as a control.

Essentially no protein binding was seen with the Pluronic® surfactants. The sorbitol mono-oleate surfactant was found to exhibit a level of protein binding substantially identical to that of the uncoated PVDF. Although not wishing to be bound by any particular theory of operation, it is believed that the results obtained with sorbitol mono-oleate are related to the short length of this molecule's philic end (i.e., approximately 5 Å). For comparison, the Pluronic® L-121, Pluronic® L-122, and Pluronic® L-123 surfactants have philic ends whose lengths are approximately 16, 36, and 61 Å, respectively. When coating a membrane having small pores and thus a larger surface area, it is believed that the length of a surfactant's philic ends may play a more important role in achieving a low binding surface than in other applications of the invention.

EXAMPLE 15

In-Mold Coating

The in-mold coating aspects of the invention were tested by molding 24-well polystyrene plates. Sorbitol mono-oleate in isopropanol was used as the non-ionic surfactant at concentrations of 0.01% (w/v) and 0.1% (w/v). The 0.01% concentration was estimated to produce less than one monolayer of surfactant on the finished product, while the 0.1% concentration produced about 7 monolayers. The surfactant was applied to the mold using a Crown sprayer (Crown Industrial Products, Hebron, Ill.; Catalog #8011), which produces a sufficiently fine spray of droplets to uniformly coat the mold. The mold was sprayed before each part was made.

The 0.1% solution produced a finished product which was clear and exhibited essentially no protein binding when tested with IgG protein and colloidal gold staining. With the 0.01% concentration, pooling and missed areas were seen which bound protein.

Concentrations above 0.1%, i.e., concentrations ranging up to 2%, were also tested and found to work successfully.

Similar experiments were performed with a 1% isopropanol solution of glycerol mono-stearate. The part again exhibited low protein binding. A 15–25% haze, however, was observed, which made the part less transparent than an uncoated part (3–5% haze). Coating with a 0.01% isopropanol solution of sorbitol tri-stearate, on the other hand, produced a part which had the same level of haze as an uncoated part, i.e., 3–5% haze. Similar results, i.e., low hazing, were achieved with a 1% solution of ethylene glycol mono-stearate and a 1% solution of sorbitol tri-oleate. It is believed that the hazing seen with the 1% solution of glycerol mono-stearate may have been due to the use of a sprayer which did not produce a sufficiently fine spray of droplets to completely coat the mold with surfactant.

Bars of polystyrene were also coated with surfactants using the in-mold process and exhibited reduced protein binding.

EXAMPLE 16

Polymer Blends

In order to demonstrate the binding effect of polymer surfaces molded from a blend containing a non-ionic surfactant, several low binding molecules and matrix polymers were blended and subsequently molded. Low binding non-ionic surfactant molecules were blended at 5% (except as noted in Table 13) into a base polymer using a twin screw extruder, then injection molded into the shape of 35 mm petri dishes. Proteins tested were BSA and Fetal Bovine Serum (FBS). Protein binding was determined using a colloidal gold staining procedure as described above. In the case of the polypropylene and EVA blends, a silver enhancer was used (Sigma Chem. Co., St, Louis, Mo., Kit# SE-100).

It was discovered that while not each non-ionic surfactant having the requisite low HLB number ($\leq 10$) was able to migrate to the surface of each base polymer in order to create a noticeable non-binding effect, a sufficient number of blends exhibited the desired non-binding characteristics to indicate that, in those instances, much of the low HLB, non-ionic surfactant had indeed bloomed to the polymer surface. The reason that some molecules having the requisite HLB number do not bloom to the surface of some polymers while others do, is not fully understood. However, such an understanding is not necessary in order to practice this embodiment of the invention.

The base or matrix polymer used for the blend may be selected from the group including ethylene vinyl acetate, polypropylene, polyolefin, polyvinylchloride, polystyrene, polystyrene-butadiene copolymer, polycarbonate, polyacrylate, polyamide, and copolymers thereof, polyurethane, polyester and copolymers thereof, and fluoropolymers.

As shown in Table 13, non ionic surfactants with HLB numbers less than 10, such as sorbitol mono-oleate (HLB= 4.3), PEO stearyl alcohol (HLB=4.7) and PEO oleyl ether (HLB=4.9) in polypropylene or EVA resulted in no detectable BSA or FBS protein binding. In contrast, the base polymers, without surfactant in the blend, readily bound the protein. In addition, blends with HLB numbers of greater than 10 showed significant protein binding and in some cases, exhibited higher protein binding than the base polymers alone.

The blends were compounded on a Leistritz 34-mm twin screw extruder, zones set at 200°–240° C., with a feed rate of 10–50 pounds per hour. Injection molding of the blends into 35 mm petri dishes was performed on a 25 ton Battenfeld molding machine, zones set at 200°–250° C.

Although preferred and other embodiments of the invention have been described herein, further embodiments may be perceived by those skilled in the art without departing from the scope of the invention as defined by the following claims.

TABLE 1

| | | Non-Sterilized | | Sterilized | |
|---|---|---|---|---|---|
| Coating | HLB NO. | TOTAL | TIGHT | TOTAL | TIGHT |
| High Binding PS (uncoated) | NA | NA | NA | 847 | 768 |
| Medium Binding PS (uncoated) | NA | 861 | 356 | NA | NA |
| BSA Protein | NA | 594 | 173 | ND | ND |
| PEO/PPO Block Copolymer, Pluronic ® L-121 | 1 | 18 | 4 | ND | ND |
| PEO/PPO Block Copolymer, Pluronic ® L-122 | 2 | 12 | 3 | ND | ND |

TABLE 1-continued

|  |  | Non-Sterilized | | Sterilized | |
| --- | --- | --- | --- | --- | --- |
| Coating | HLB NO. | TOTAL | TIGHT | TOTAL | TIGHT |
| PEO/PPO Block Copolymer, Pluronic ® P-123 | 7 | 7 | 2 | ND | ND |
| PEO/PPO Block Copolymer, Pluronic ® F-127 | 18 | ND | 2 | ND | ND |
| PEO(2) CETYL ETHER | 5.3 | 18 | 11 | 54 | 25 |
| PEO(4) LAURYL ETHER | 9.7 | 2 | 2 | 10 | 4 |
| PEO(2) OLEYL ETHER | 4.9 | 7 | 5 | 22 | 4 |
| PEO(4) SORBITOL MONO-LAURATE | 13.3 | 4 | 2 | 5 | 3 |
| PEO(4) SORBITOL MONO-STEARATE | 9.6 | 37 | 18 | 130 | 80 |
| PEO(20) SORBITOL TRI-STEARATE | 10.5 | 5 | 2 | 7 | 4 |
| PEO(8)STEARATE | 11.1 | 6 | 3 | 15 | 9 |
| PEO(2) STEARYL ETHER | 4.9 | 83 | 28 | 36 | 17 |
| SORBITOL MONO-OLEATE | 4.3 | 31 | 7 | 33 | 5 |

TABLE 2

| Coating | HLB No. | % Reduction in Protein Binding |
| --- | --- | --- |
| High Binding PS - (uncoated) | NA | 0.0 |
| Medium Binding PS - (uncoated) | NA | 50.0 |
| GLYCEROL MONO-OLEATE | 3.4 | 92.4 |
| PEO(2) CETYL ETHER | 5.3 | 99.9 |
| PEO(4) LAURYL ETHER | 9.7 | 99.3 |
| PEO(2) OLEYL ETHER | 4.9 | 99.9 |
| PEO(4) SORBITOL MONO-LAURATE | 13.3 | 99.8 |
| PEO(4) SORBITOL MONO-STEARATE | 9.6 | 99.5 |
| PEO(20) SORBITOL TRI-STEARATE | 10.5 | 99.7 |
| PEO(8) STEARATE | 11.1 | 99.1 |
| PEO(2) STEARYL ETHER | 4.9 | 97.9 |
| SORBITOL MONO-OLEATE | 4.3 | 92.7 |
| SORBITOL MONO-PALMITATE | 6.7 | 88.9* |
| SORBITOL MONO-STEARATE | 4.7 | 83.1* |

TABLE 3

| Coating | HLB No. | IgG Protein Binding Absorbance (550 nm) |
| --- | --- | --- |
| Medium Binding PS | NA | 0.15 |
| PEO(2) CETYL ETHER | 5.3 | 0.00 |
| PEO(4) LAURYL ETHER | 9.7 | 0.00 |
| PEO(2) OLEYL ETHER | 4.9 | 0.00 |
| PEO(4) SORBITOL MONO-LAURATE | 13.3 | 0.00 |
| PEO(4) SORBITOL MONO-STEARATE | 9.6 | 0.00 |
| PEO(20) SORBITOL TRI-STEARATE | 10.5 | 0.00 |
| PEO(8) STEARATE | 11.1 | 0.00 |
| PEO(2) STEARYL ETHER | 4.9 | 0.00 |
| SORBITOL MONO-LAURATE | 8.6 | 0.00 |
| SORBITOL MONO-OLEATE | 4.3 | 0.00 |
| SORBITOL MONO-PALMITATE | 6.7 | 0.00 |
| SORBITOL MONO-STEARATE | 4.7 | 0.00 |

TABLE 4

| | | Absorbance (550 nm) | | |
| --- | --- | --- | --- | --- |
| Coating | HLB No. | pH = 4.6 | pH = 7.4 | pH = 9.2 |
| PS (uncoated) | NA | 0.08 | 0.10 | 0.12 |
| PEO(2) CETYL ETHER | 5.3 | 0.00 | 0.00 | 0.00 |
| PEO(4) LAURYL ETHER | 9.7 | 0.00 | 0.00 | 0.00 |
| PEO(2) OLEYL ETHER | 4.9 | 0.00 | 0.00 | 0.00 |
| PEO(4) SORBITOL MONO-STEARATE | 9.6 | 0.00 | 0.00 | 0.00 |
| PEO(20) SORBITOL TRI-STEARATE | 10.5 | 0.00 | 0.00 | 0.00 |
| PEO(8) STEARATE | 11.1 | 0.00 | 0.00 | 0.00 |
| PEO(2) STEARYL ETHER | 4.9 | 0.00 | 0.00 | 0.00 |
| SORBITOL MONO-LAURATE | 8.6 | 0.00 | 0.00 | 0.00 |
| SORBITOL MONO-OLEATE | 4.3 | 0.00 | 0.00 | 0.00 |
| SORBITOL MONO-PALMITATE | 6.7 | 0.00 | 0.00 | 0.00 |
| SORBITOL MONO-STEARATE | 4.7 | 0.00 | 0.00 | 0.00 |

TABLE 5

| Coating | HLB No. | MDCK Attachment | Visual Color Upon Protein Staining |
|---|---|---|---|
| PS (uncoated) | NA | Many attached and extended cells | Very Dark |
| Covalently attached photo-acrylamide coating (Corning Costar catalog #2500) | NA | None | ND because Au stain binds to acrylamide coaling |
| STEARIC ACID | | Many attached and extended cells | Very dark |
| PEO(2) CETYL ETHER | 5.3 | ND | None |
| PEO(4) LAURYL ETHER | 9.7 | None | None |
| PEO(2) OLEYL ETHER | 4.9 | ND | None |
| PEO(20) SORBITOL MONO-LAURATE | 16.6 | None | None |
| PEO/PPO Block Copolymer Pluronic ® L-121 | 1 | None | None |
| PEO(4) SORBITOL MONO-STEARATE | 9.6 | None | None |
| PEO(20) SORBITOL TRI-STEARATE | 10.5 | None | None |
| PEO(8) STEARATE | 11.1 | Coating was uneven; could not see cells | None in most areas; a few splotchy areas |
| SORBITOL MONO-OLEATE | 4.3 | Slight; coating may have been uneven | None in most areas; a few splotchy areas |
| SORBITOL MONO-PALMITATE | 6.7 | None | None |
| SORBITOL MONO-STEARATE | 4.7 | Coating was uneven; did not appear to have cells attached | None in most areas; a few splotchy areas |

TABLE 6

| Coating | HLB No. | Type of Endgroups | Bound Protein Absorbance at 550 nm |
|---|---|---|---|
| PS (uncoated) | NA | Uncoated | 0.10 |
| PEO/PPO Block Copolymer, Pluronic ® L-121 | 1 | Philic (both) | 0.00 |
| PEO/PPO Block Copolymer, Pluronic ® L-122 | 2 | Philic (both) | 0.00 |
| PEO/PPO Block Copolymer, Pluronic ® P-123 | 7 | Philic (both) | 0.00 |
| PEO(2) CETYL ETHER | 5.3 | Philic (one) | 0.00 |
| PEO(200) DI-OLEATE | 5.0 | Phobic (both) | 0.15 |
| PEO(400) DI-OLEATE | 8.5 | Phobic (both) | 0.15 |
| PEO(400) DI-STEARATE | 8.8 | Phobic (both) | 0.10 |
| PEO(600) DI-STEARATE | 10.6 | Phobic (both) | 0.10 |
| PEO(2) OLEYL ETHER | 4.9 | Philic (one) | 0.00 |
| PEO(4) SORBITOL MONO-LAURATE | 13.3 | Philic (one) | 0.00 |
| PEO(20) SORBITOL TRI-STEARATE | 10.5 | Philic (one) | 0.00 |
| POLYPROPYLENE OXIDE (4,000 M.W.) | <0.5 | Philic (two) | 0.00 |
| SORBITOL MONO-OLEATE | 4.3 | Philic (one) | 0.00 |

TABLE 7

| Coating | HLB No. | Absorbance (550 nm) Dried before H$_2$O rinse | Absorbance (550 nm) H$_2$O rinsed before drying |
|---|---|---|---|
| PS (uncoated) | NA | 0.13–0.15 | 0.13–0.15 |
| PEO/PPO Block Copolymer, Pluronic ® L-121 | 1 | 0.00 | 0.13–0.16 |
| PEO/PPO Block Copolymer, Pluronic ® L-122 | 2 | 0.00 | 0.12–0.15 |
| PEO/PPO Block Copolymer, Pluronic ® P-123 | 7 | 0.08–0.11 | 0.14–0.16 |
| PEO/PPO, Block Copolymer, Pluronic ® F-127 | 18 | 0.13–0.16 | 0.13–0.16 |
| PEO(4) LAURYL ETHER | 9.7 | 0.08–0.10 | 0.13–0.16 |

TABLE 7-continued

| Coating | HLB No. | Absorbance (550 nm) Dried before H₂O rinse | Absorbance (550 nm) H₂O rinsed before drying |
|---|---|---|---|
| PEO(2) OLEYL ETHER | 4.9 | 0.00 | 0.14–0.16 |
| PEO(20) SORBITOL MONO-LAURATE | 16.6 | 0.14–0.16 | 0.13–0.16 |

TABLE 8

| | | Absorbance (405 nm) | | | |
|---|---|---|---|---|---|
| | | High Binding Polystrene | | Medium Binding Polystyrene | |
| Surfactant | HLB No. | No Rinse | Rinsed | No Rinse | Rinsed |
| None | NA | 2.00 | 2.10 | 1.90 | 1.90 |
| PEO/PPO Block Copolymer, Pluronic ® L-121 | 1 | 0.00 | 1.90 | 0.00 | 1.00 |
| PEO/PPO Block Copolymer, Pluronic ® L-122 | 2 | 0.00 | 1.90 | 0.00 | 1.70 |
| PEO/PPO Block Copolymer, Pluronic ® P-123 | 7 | 0.00 | 1.80 | 0.00 | 1.70 |
| PEO/PPO Block Copolymer, Pluronic ® F-127 | 18 | 0.00 | 1.00 | 0.00 | 1.40 |
| PEO(4) LAURYL ETHER | 9.7 | ND | 2.10 | ND | 1.90 |
| PEO(2) OLEYL ETHER | 4.9 | ND | 2.10 | ND | 1.90 |
| PEO(20) SORBITOL MONO-LAURATE | 16.6 | 0.00 | 2.00 | 0.00 | 1.90 |

TABLE 9

| | | Absorbance (550 nm) | | | | | |
|---|---|---|---|---|---|---|---|
| Coating | HLB No. | Initial | 1 Time 1 hr 23° C. | 1 Time 24 hr 23° C. | 1 Time 24 hr 37° C. | 1 Time 24 hr 70° C. | 6 Times 30 min each 23° C. |
| PS (uncoated) | NA | 0.10 | 0.10 | 0.10 | 0.10 | 0.10 | 0.10 |
| PEO/PPO Block Copolymer, Pluronic ® L-121 | 1 | 0.00 | 0.00 | 0.00 | 0.00 | 0.00 | 0.00 |
| PEO/PPO Block Copolymer, Pluronic ® L-122 | 2 | 0.00 | 0.00 | 0.00 | 0.00 | 0.00 | 0.00 |
| PEO/PPO Block Copolymer, Pluronic ® P-123 | 7 | 0.00 | 0.00 | 0.00 | 0.00 | 0.00–0.03 | 0.02–0.06 |
| PEO/PPO Block Copolymer, Pluronic ® F-127 | 18 | 0.00 | 0.05–0.10 | 0.10 | 0.10 | 0.10 | 0.10 |
| PEO(4) SORBITOL MONO-LAURATE | 13.3 | 0.00 | 0.09 | 0.10 | 0.10 | 0.10 | 0.10 |
| PEO(20) SORBITOL MONO-LAURATE | 16.6 | 0.00 | 0.02 | 0.05 | 0.10 | 0.10 | 0.10 |
| PEO(4) SORBITOL MONO-STEARATE | 9.6 | 0.00 | 0.00 | 0.02 | 0.10 | 0.10 | 0.10 |
| PEO(20) SORBITOL TRI-STEARATE | 10.5 | 0.00 | 0.00 | 0.02 | 0.10 | 0.10 | 0.10 |
| SORBITOL MONO-LAURATE | 8.6 | 0.00 | 0.00 | 0.00 | 0.00 | 0.00–0.02 | 0.02–0.06 |
| SORBITOL MONO-OLEATE | 4.3 | 0.00 | 0.00 | 0.00 | 0.00 | 0.00 | 0.00 |
| SORBITOL MONO-PALMITATE | 6.7 | 0.00 | 0.00 | 0.00 | 0.00 | 0.00 | 0.02–0.06 |
| SORBITOL MONO-STEARATE | 4.7 | 0.00 | 0.00 | 0.00 | 0.00 | 0.00 | 0.00 |
| SORBITOL TRI-OLEATE | 1.8 | 0.00 | 0.00 | 0.00 | 0.00 | 0.00 | 0.00 |

TABLE 10

| Coating | HLB No. | Absorbance (550 nm) | | | |
|---|---|---|---|---|---|
| | | Polystyrene | Polypropylene | Polymethyl Methacrylate | KYNAR ® Flex 2800 PVDF copolymer |
| As Molded Not Coated | NA | 0.10 | 0.08 | 0.15 | 0.15 |
| PEO/PPO Block Copolymer, Pluronic ® L-31 | 6–7 | 0.0–0.2 | 0.04 | 0.02–0.04 | 0.04–0.12 |
| PEO/PPO Block Copolymer, Pluronic ® L-62 | 5–6 | ND | 0.04 | 0.02 | 0.02–0.08 |
| PEO/PPO Block Copolymer, Pluronic ® L-64 | 15 | ND | 0.08 | 0.02 | 0.02–0.08 |
| PEO/PPO Block Copolymer, Pluronic ® L-121 | 1 | 0.00 | 0.00 | 0.00 | 0.00 |
| PEO/PPO Block Copolymer, Pluronic ® L-122 | 2 | 0.00 | 0.00 | 0.00 | 0.00 |
| PEO/PPO Block Copolymer, Pluronic ® P-123 | 7 | 0.02–0.04 | 0.03 | 0.01 | 0.02–0.08 |
| PEO/PPO, Block Copolymer, Pluronic ® F-127 | 18 | 0.07–0.10 | 0.04–0.08 | 0.02–0.08 | 0.06 |
| SORBITOL MONO-OLEATE | 4.3 | 0.00 | 0.00 | ND | ND |

TABLE 11

| Number of Exposures | Total Exposure Time (min) | Ratio of Weight of Protein to Weight of Coating | Absorbance at 550 nm | Absorbance of Uncoated Polystyrene Control |
|---|---|---|---|---|
| 1 | 30 | 80 | 0.0 | 0.10 |
| 2 | 60 | 160 | 0.0 | 0.10 |
| 3 | 90 | 240 | 0.0 | 0.10 |
| 4 | 120 | 320 | 0.0 | 0.10 |
| 5 | 150 | 400 | 0.0 | 0.10 |
| 6 | 180 | 480 | 0.0 | 0.10 |

TABLE 12

| Molecule | HLB No. | $LD_{50}$ grams/Kg (rat) |
|---|---|---|
| PEO(4) LAURYL ETHER | 9.7 | >5 |
| PEO(4) SORBITOL MONO-LAURATE | 13.3 | >38 |
| PEO(20) SORBITOL TRI-STEARATE | 10.5 | >39 |
| PEO(8) STEARATE | 11.1 | >31 |
| PEO(2) STEARYL ETHER | 4.9 | >25 |
| SORBITOL MONO-OLEATE | 4.3 | >39 |
| SORBITOL MONO-STEARATE | 4.7 | >15 |
| SORBITOL TRI-STEARATE | 2.1 | >15 |
| MINERAL OIL | NA | 22 |
| NaCl | NA | 4 |
| $As_2O_3$ | NA | 0.02 |

TABLE 13

| Blended Molecule | Base Polymer | HLB # | Bound Protein Absorbance (550 nm) | |
|---|---|---|---|---|
| | | | BSA | FBS |
| None (control) | polypropylene | N/A | 0.092 | 0.140 |
| PEO(2) OLEYL ETHER | polypropylene | 4.9 | 0.000 | 0.000 |
| PEO(2) STEARYL ETHER | polypropylene | 4.9 | 0.000 | 0.000 |
| SORBITOL MONO-STEARATE | polypropylene | 4.7 | 0.000 | 0.000 |
| SORBITOL MONO-OLEATE | polypropylene | 4.3 | 0.000 | 0.000 |
| SORBITOL TRI-OLEATE | polypropylene | 1.8 | 0.000 | 0.000 |
| PEO/PPO Block Copolymer, Pluronic ® L-121 | polypropylene | 1.0 | 0.029 | 0.144 |
| PEO(4) SORBITOL MONO-STEARATE | polypropylene | 9.6 | 0.016 | 0.057 |

TABLE 13-continued

| Blended Molecule | Base Polymer | HLB # | Bound Protein Absorbance (550 nm) | |
| --- | --- | --- | --- | --- |
| | | | BSA | FBS |
| PEO(4) SORBITOL MONO-LAURATE | polypropylene | 13.3 | 0.060 | 0.056 |
| PEO(20) SORBITOL MONO-LAURATE | polypropylene | 16.7 | 0.153 | 0.270 |
| PEO/PPO Block Copolymer, Pluronic ® F-127 | polypropylene | 18 | 0.202 | 0.250 |
| PEO/PPO Block Copolymer, Pluronic ® F-68 | polypropylene | >24 | 0.094 | 0.358 |
| None (control) | ethylene vinyl acetate | N/A | 0.305 | 0.532 |
| PEO(2) OLEYL ETHER | ethylene vinyl acetate | 4.9 | 0.000 | 0.000 |
| 1% PEO(2) OLEYL ETHER | ethylene vinyl acetate | 4.9 | 0.000 | 0.291 |
| SORBITOL MONO-OLEATE | ethylene vinyl acetate | 4.3 | 0.000 | 0.000 |
| 1% SORBITOL MONO-OLEATE | ethylene vinyl acetate | 4.3 | 0.147 | 0.371 |
| PEO/PPO Block Copolymer, Pluronic ® L-121 | ethylene vinyl acetate | 1 | 0.000 | N/A |
| none | polystyrene (control) | N/A | 0.215 | 0.138 |
| PEO(2) OLEYL ETHER | polystyrene | 4.9 | 0.007 | 0.015 |
| PEO(2) STEARYL ETHER | polystyrene | 4.9 | 0.008 | 0.009 |
| SORBITOL TRI-STEARATE | polystyrene | 2.1 | 0.005 | 0.008 |
| PEO/PPO Block Copolymer, Pluronic ® F-127 | polystrene | 1.8 | 0.250 | N/A |
| PEO/PPO Block Copolymer, Pluronic ® F-68 | polystrene | >24 | 0.094 | 0.358 |

TABLE 14

| Molecule | HLB No. | Tradename |
| --- | --- | --- |
| ETHYLENE GLYCOL MONO-STEARATE | 3.0 | Emerest ® 2350 |
| GLYCEROL MONO-OLEATE | 3.4 | Emerest ® 2421 |
| GLYCEROL MONO-STEARATE | 3.4 | Emerest ® 2400 |
| PEO/PPO Block Copolymer | 6-7 | Pluronic ® L-31 |
| PEO/PPO Block Copolymer | 4 | Pluronic ® L-61 |
| PEO/PPO Block Copolymer | 5 | Pluronic ® L-62 |
| PEO/PPO Block Copolymer | 15 | Pluronic ® L-64 |
| PEO/PPO Block Copolymer | 1 | Pluronic ® L-121 |
| PEO/PPO Block Copolymer | 2 | Pluronic ® L-122 |
| PEO/PPO Block Copolymer | 7 | Pluronic ® P-123 |
| PEO/PPO Block Copolymer | 18 | Pluronic ® F-127 |
| PEO(2) CETYL ETHER | 5.3 | Brij ® 52 |
| PEO(200) DI-OLEATE | 5.0 | Maypeg ® 200 DO |
| PEO(400) DI-OLEATE | 8.5 | Maypeg ® 400 DO |
| PEO(400) DI-STEARATE | 8.8 | Maypeg ® 400 DS |
| PEO(600) DI-STEARATE | 10.6 | Maypeg ® 400 DS |
| PEO(4) LAURYL ETHER | 9.7 | Brij ® 30 |
| PEO(200) MONO-OLEATE | 8.3 | Emerest ® 2624 |
| PEO(2) OLEYL ETHER | 4.9 | Brij ® 93 |
| PEO(4) SORBITOL MONO-LAURATE | 13.3 | Tween ® 21 |
| PEO(20) SORBITOL MONO-LAURATE | 16.6 | Tween ® 20 |
| PEO(4) SORBITOL MONO-STEARATE | 9.6 | Tween ® 61 |
| PEO(20) SORBITOL TRI-STEARATE | 10.5 | Tween ® 65 |
| PEO(8) STEARATE | 11.1 | Myrj ® 45 |
| PEO(2) STEARYL ETHER | 4.9 | Brij ® 72 |
| POLYPROPYLENE OXIDE (4,000 M.W.) | <0.5 | Purchased from Aldrich, Milwaukee, WI |
| SORBITOL MONO-LAURATE | 8.6 | SPAN ® 20 |
| SORBITOL MONO-OLEATE | 4.3 | SPAN ® 80 |
| SORBITOL MONO-PALMITATE | 6.7 | SPAN ® 40 |
| SORBITOL MONO-STEARATE | 4.7 | SPAN ® 60 |
| SORBITOL TRI-OLEATE | 1.8 | SPAN ® 85 |
| SORBITOL TRI-STEARATE | 2.1 | SPAN ® 65 |

Brij® is a registered trademark of ICI Americas, Wilmington, Del.

Emerest® is a registered trademark of Henkel Corp., Cincinnati, Ohio

Maypeg® is a registered trademark of PPG Industries, Gurnee, Ill.

Myrj® is a registered trademark of ICI Americas, Wilmington, Del.

Pluronic® is a registered trademark of BASF, Parsippany, N.J.

Span® is a registered trademark of ICI Americas, Wilmington, Del.

Tween® is a registered trademark of ICI Americas, Wilmington, Del.

What is claimed is:

1. A method for treating a hydrophobic surface so as to reduce the ability of an organic material in an aqueous solution to bind to the surface, said method comprising:
   (a) applying a coating solution to the hydrophobic surface, said coating solution comprising a non-ionic surfactant in a solvent, said non-ionic surfactant having (i) a hydrophilic-lipophilic balance number which is less than or equal to 5 and (ii) at least one hydrophilic element which can extend into an aqueous solution; and
   (b) drying the coated hydrophobic surface of step (a) to remove the solvent from the coating solution and thereby bind the non-ionic surfactant to the hydrophobic surface;
   said applying and drying steps being performed without an intermediate washing step with an organic solvent and without a previous or subsequent glow discharge treatment.

2. The method of claim 1 comprising the additional step after step (b) of contacting the treated surface with an aqueous solution containing the organic material, said treated surface exhibiting reduced binding of the organic material in comparison to an untreated surface.

3. The method of claim 2 wherein the treated surface exhibits a level of binding of the organic material which is less than 0.5 times the level of binding exhibited by an untreated surface.

4. The method of claim 2 wherein the treated surface exhibits a level of binding of the organic material which is less than 0.3 times the level of binding exhibited by an untreated surface.

5. The method of claim 1 comprising the additional step after step (b) of contacting the treated surface with an aqueous solution containing the organic material for a period of time, said organic material having biological activity and exhibiting enhanced retention of its biological activity when the aqueous solution is in contact with the treated surface than when the aqueous solution is in contact with an untreated surface over said period of time.

6. The method of claim 5 wherein the period of time is 90 minutes and the organic material exhibits a retention of biological activity when the aqueous solution is in contact with the treated surface which is at least 1.5 times the retention of biological activity when the aqueous solution is in contact with an untreated surface.

7. The method of claim 1 wherein the non-ionic surfactant has a hydrophilic-lipophilic balance number which is less than or equal to 2.5.

8. The method of claim 7 wherein the non-ionic surfactant comprises an ethylene oxide/propylene oxide block co-polymer.

9. The method of claim 7 wherein the non-ionic surfactant comprises polypropylene oxide.

10. The method of claim 1 wherein the solvent comprises an alcohol.

11. The method of claim 1 wherein the hydrophobic surface is a polymeric surface.

12. The method of claim 11 wherein the polymeric surface comprises polystyrene.

13. The method of claim 1 wherein the organic material is a protein, a peptide, a nucleic acid, or a cell.

14. The method of claim 1 wherein the organic material is an enzyme or an antibody.

15. The method of claim 1 wherein the organic material exhibits at least some hydrophobicity in an aqueous solution.

16. Apparatus comprising a hydrophobic surface which has been treated in accordance with the method of claim 1.

17. The apparatus of claim 16 wherein the apparatus comprises labware.

18. A hydrophobic surface treated in accordance with the method of claim 1.

19. The treated surface of claim 18 wherein the non-ionic surfactant has a hydrophilic-lipophilic balance number which is less than or equal to 2.5.

20. The treated surface of claim 18 wherein the non-ionic surfactant comprises an ethylene oxide/propylene oxide block co-polymer.

21. The treated surface of claim 18 wherein the non-ionic surfactant comprises polypropylene oxide.

22. The treated surface of claim 18 wherein the hydrophobic surface is a polymeric surface.

23. The treated surface of claim 22 wherein the polymeric surface comprises polystyrene.

* * * * *